(12) United States Patent
Qiu

(10) Patent No.: US 10,631,573 B2
(45) Date of Patent: Apr. 28, 2020

(54) ATOMIZER AND AEROSOL GENERATING DEVICE USING THE SAME

(71) Applicant: CHANGZHOU JWEI INTELLIGENT TECHNOLOGY CO., LTD., Changzhou (CN)

(72) Inventor: Wei-Hua Qiu, ChangZhou (CN)

(73) Assignee: CHANGZHOU JWEI INTELLIGENT TECHNOLOGY CO., LTD., Changzhou (CN)

( * ) Notice: Subject to any disclaimer, the term of this patent is extended or adjusted under 35 U.S.C. 154(b) by 90 days.

(21) Appl. No.: 15/806,604

(22) Filed: Nov. 8, 2017

(65) Prior Publication Data

US 2018/0064172 A1 Mar. 8, 2018

Related U.S. Application Data

(63) Continuation-in-part of application No. PCT/CN2016/086294, filed on Jun. 17, 2016.

(30) Foreign Application Priority Data

Jun. 19, 2015 (CN) ...................... 2015 2 0431327 U

(51) Int. Cl.
*A24F 47/00* (2020.01)
*A61M 15/06* (2006.01)
(Continued)

(52) U.S. Cl.
CPC ............ *A24F 47/008* (2013.01); *A24F 47/00* (2013.01); *A61M 11/042* (2014.02); *A61M 15/06* (2013.01); *B05B 7/26* (2013.01)

(58) Field of Classification Search
CPC ...... A24F 47/008; A24F 47/00; A24F 47/002; A61M 1/042; B05B 7/26; B05B 11/06
See application file for complete search history.

(56) References Cited

U.S. PATENT DOCUMENTS 3,561,444 A * 2/1971 Boucher ........... A61M 15/0085
128/200.16
4,427,004 A * 1/1984 Miller .................... A61M 11/06
128/200.21
(Continued)

FOREIGN PATENT DOCUMENTS

CN 104203018 A 12/2014
CN 104207330 A 12/2014
(Continued)

*Primary Examiner* — Steven J Ganey
*Assistant Examiner* — Tuongminh N Pham
(74) *Attorney, Agent, or Firm* — ScienBizi, P.C.

(57) ABSTRACT

An atomizer for an electronic cigarette includes an atomizing assembly, an adjusting assembly, a bottom cover, and a collecting device. The collecting device and the atomizing assembly are arranged on the bottom cover. The adjusting assembly includes a substrate with an injecting hole and an adjusting member. Size of the injecting hole is adjustable by rotating the adjusting member. The present application also provides another embodiment, which includes an atomizing assembly with an atomizer head and an air inlet pipe, and an adjusting assembly with an air inlet in fluid communication with the outside. One end of the air inlet pipe is communicated with the bottom of the atomizer head, and the other end of the air inlet pipe is in fluid communication with the air inlet. The atomizers have an anti-leakage function. The present application also provides an aerosol generating device with the atomizer.

15 Claims, 8 Drawing Sheets

(51) Int. Cl.
*A61M 11/04* (2006.01)
*B05B 7/26* (2006.01)

(56) References Cited

U.S. PATENT DOCUMENTS

| | | | |
|---|---|---|---|
| 5,687,746 | A | 11/1997 | Rose et al. |
| 2014/0261500 | A1 | 9/2014 | Park |
| 2016/0219935 | A1 | 8/2016 | Qiu |
| 2017/0347705 | A1* | 12/2017 | Li ........................ A24F 47/008 |

FOREIGN PATENT DOCUMENTS

| | | |
|---|---|---|
| CN | 204217908 U | 3/2015 |
| CN | 104544575 A | 4/2015 |
| CN | 204393353 U | 6/2015 |
| GB | 2412876 A | 10/2005 |

* cited by examiner

ATOMIZER AND AEROSOL GENERATING DEVICE USING THE SAME

CROSS-REFERENCE TO RELATED APPLICATIONS

The subject matter herein generally relates to atomizers and aerosol generating devices using the atomizers. This application is a continuation application of PCT patent application Serial Number PCT/CN2016/086294, filed on Jun. 17, 2016, which claims priority to CN Patent Application Serial Number 201520431327.4, filed on Jun. 19, 2015, the disclosure of which is incorporated herein by reference.

FIELD

The subject matter herein generally relates to atomizers and aerosol generating devices using atomizers.

BACKGROUND

At present, an electronic cigarette existing on the market universally has a leakage problem. Reasons of the leakage problem include many aspects, and a main reason is that smoke liquid easily leaks from a storage chamber through an atomizing assembly. After the smoke liquid leaks, on one hand, a user may taste the smoke liquid during smoking, which would affect the user's smoking experience. On the other hand, the smoke liquid may also contaminate a battery and/or a control panel, which would affect a normal working of the electronic cigarette.

A leak-proof structure to prevent the leakage of the smoke liquid is complex and of poor reliability.

SUMMARY

The present disclosure provides an atomizer and an aerosol generating devices using the atomizer.

An atomizer includes an atomizing assembly, an adjusting assembly arranged on the atomizing assembly, a bottom cover, and a collecting device. The atomizing assembly is arranged on the bottom cover, and the collecting device is arranged between the bottom cover and the atomizing assembly. The adjusting assembly includes a substrate and an adjusting member movably related to the substrate. The substrate defines an injecting hole, and an area of the air inlet in fluid communication with outside is changed by movement of the adjusting member.

In an alternative embodiment, the adjusting member includes an adjusting window in fluid communication with the injecting hole, and the injecting hole is shielded or exposed through the adjusting window when the adjusting member is in rotation.

In an alternative embodiment, the atomizing assembly further includes an air inlet channel and an atomizing chamber in fluid communication with the air inlet channel. The substrate defines at least one air inlet corresponding to the adjusting window, and the air inlet is in fluid communication with the air inlet channel. The air inlet is shielded or exposed through the adjusting window when the adjusting member is in rotation.

In an alternative embodiment, the adjusting member is an adjusting ring rotatably sleeved on the substrate.

In an alternative embodiment, the adjusting member is an adjusting sheet latched on an edge or inner of the substrate. The adjusting sheet is rotable along the edge or inner of the substrate, and the injecting hole and/or the air inlet are shielded or exposed when the adjusting sheet is in rotation.

In an alternative embodiment, the collecting device includes a stagnating portion, a tube, and a collecting slot. The stagnating portion extends from one end of the tube toward an inside of the tube. The stagnating portion is fixedly coupled with the tube to form the collecting slot. An angle formed between the tube and the stagnating portion is substantially in a range from 0 to 90 degrees.

In an alternative embodiment, the stagnating portion is substantially in a shape of a bowl or a funnel.

In an alternative embodiment, the substrate comprises a main body, an inner tube, a separator, and a splitter plate. The separator is laminated on the splitter plate. The separator and the splitter plate are arranged between the main body and the inner tube. The separator and the splitter plate are fixedly coupled with the body and the inner tube, respectively. The injecting hole penetrates through the main body, through a part of a laminated area formed between the separator and the splitter plate, and through the inner tube.

In an alternative embodiment, the air inlet is defined on the main body, and the inner tube separates the air inlet and the injecting hole.

An aerosol generating device includes any one of the above mentioned atomizer.

An atomizer includes an atomizing assembly, and an adjusting assembly arranged on an upper end of the atomizing assembly. The atomizing assembly includes an atomizer head and an air inlet pipe. The adjusting assembly comprises an air inlet in fluid communication with the outside. One end of the air inlet pipe is in fluid communication with a bottom of the atomizer head, and the other end of the air inlet pipe is in fluid communication with the air inlet.

In an alternative embodiment, the atomizing assembly further comprises a base, and the base is disposed with a connecting tube and a through hole in fluid communication with the connecting tube. The bottom of the atomizer head defines a ventilating hole in fluid communication with the through hole. One end of the air inlet pipe is sleeved within the connecting tube. The air inlet pipe is in fluid communication with the ventilating hole by the through hole. Air enters the air inlet pipe through the air inlet, and then enters the atomizer head through the connecting tube, the through hole, and the ventilating hole.

In an alternative embodiment, the adjusting assembly further includes a substrate. The substrate defines a mounting hole and the air inlet. The mounting hole is in fluid communication with the air inlet, and the other end of the air inlet pipe is mounted in the mounting hole.

In an alternative embodiment, the adjusting assembly further includes an adjusting member rotatably related to the substrate. The adjusting member includes an adjusting window. The air inlet is shielded by the adjusting member or exposed through the adjusting window, when the adjusting member is in rotation.

In an alternative embodiment, the atomizing assembly further includes an accommodating chamber for accommodating an aerosol-forming substrate. The substrate defines an injecting hole opposite to the air inlet. The injecting hole is in fluid communication with the accommodating chamber, and the injecting hole is shielded by the adjusting member or exposed through the adjusting window during the adjusting member in rotation.

In an alternative embodiment, the substrate includes a main body, an inner tube, a separator, and a splitter plate. The inner tube is located in the main body. The separator is laminated on the splitter plate, the separator and the splitter plate are arranged between the main body and the inner tube, and the separator and the splitter plate are fixedly coupled with the body and the inner tube, respectively. The air inlet is defined in the main body. The mounting hole is defined in the splitter plate. An air inlet channel is formed among the main body, the inner tube, the separator, and the splitter plate. The air inlet channel is in fluid communication with the air inlet and the mounting hole. The injecting hole penetrates through the main body, through a part of a laminated area formed between the separator and the splitter plate, and through the inner tube.

In an alternative embodiment, the atomizing assembly further includes a connecting ring. An inside of the connecting ring is coupled to the atomizer head, and an outside of the connecting ring is coupled to the base.

In an alternative embodiment, the atomizer further includes a bottom cover and a collecting device. The bottom cover is arranged on a bottom end of the atomizer head. The collecting device is arranged on the bottom cover and located between the bottom cover and the atomizer head. The collecting device comprises a stagnating portion, a tube, and a collecting slot. One end of the tube extends to an inside of the tube to form the stagnating portion. The stagnating portion is fixedly coupled with the tube to form the collecting slot. An angle formed between the tube and the stagnating portion is substantially in a range from 0 to 90 degrees.

In an alternative embodiment, the stagnating portion is substantially in a shape of a bowl or a funnel.

An aerosol generating device includes any one of the above mentioned atomizer.

The atomizer and the aerosol generating device have following advantages:

First, the adjusting assembly has functions for air intake, liquid injection, regulating the air inlet volume and the like, so as to simplify a structure of the atomizer and shorten a length of the atomizer.

Second, the adjusting assembly is located at a top end of the atomizer at a position close to an inhaler. That is, air enters the atomizer through an air inlet arranged on the top end of the atomizer, rather than through a conventional air inlet arranged on a bottom end of the atomizer, so the bottom end of the atomizer of the present application need not to define an air inlet. That is, the bottom end of the atomizer is sealed, so the aerosol-forming substrate is prevented from leaking out.

Third, liquid is injected into a top end of the atomizer through the injecting hole, a leakage problem caused by a detachable connection between the atomizing assembly and the bottom cover is avoided.

Fourth, the atomizer has a simple structure, and the device is not complex to be leak-proof.

Fifth, the atomizer has the air inlet and the injecting hole arranged on the top end of the atomizer, so the leakage of the atomizer can be avoided.

Sixth, the collecting device can further avoid the leakage of the atomizer.

BRIEF DESCRIPTION OF THE DRAWINGS

Implementations of the present technology will now be described, by way of example only, with reference to the attached figures.

Figure 1:
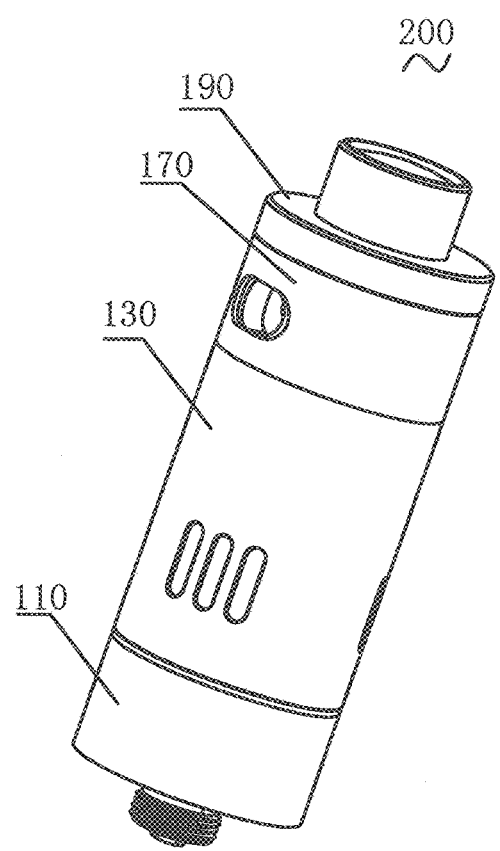
FIG. 1 is a schematic view of an atomizer, in accordance with an exemplary embodiment of the present application.

In this disclosure, 200 represents an atomizer, 1451 represents a liquid inlet, 110 represents a bottom cover, 1377 represents a connecting tube, 150 represents a conductive assembly, 111 represents a connecting hole, 170 represents a adjusting assembly, 151 represents a positive contacting member, 135 represents an accommodating chamber, 153 represents an insulating member, 137 represents a base, 171 represents a substrate, 139 represents an air inlet pipe, 173 represents an adjusting member, 141 represents a connecting ring, 1711 represents a main body, 143 represents an atomizing chamber, 1713 represents an inner tube, 145 represents an atomizer head, 1715 represents a separator, 147 represents an outer tube, 1717 represents an air inlet, 149 represents a seal ring, 1719 represents a mounting hole, 1371 represents a shoulder, 1721 represents an injecting hole, 1373 represents a first connecting portion, 210 represents a collecting device, 1375 represents a second connecting portion, 211 represents an engaging hole, 1453 represents a ventilating hole, 213 represents a stagnating portion, 215 represents a tube, 217 represents a collecting slot, 130 represents an atomizing assembly, 131 represents an accommodating tube, 133 represents an atomizing tube, 1471 represents an observing window, 1379 represents a through hole, 1716 represents a splitter plate, 1718 represents an air inlet channel, 190 represents a cigarette holder base, 191 represents a smoke outlet tube, 193 represents a cover body, and 1731 represents an adjusting window.

DETAILED DESCRIPTION

In order to make the above-mentioned objects, features and advantages of the present application more obvious, a detailed description of specific embodiments of the present application will be described in detail with reference to the accompanying drawings. A number of specific details are set forth in the following description so as to fully understand the present application. However, the present application can be implemented in many other ways different from those described herein, and those skilled in the art can make similar improvements without violating the contents of the present application. Therefore, the present application is not to be considered as limiting the scope of the embodiments described herein.

Several definitions that apply throughout this disclosure will now be presented.

The term "coupled" is defined as coupled, whether directly or indirectly through intervening components, and is not necessarily limited to physical connections. The connection may be such that the objects are permanently coupled or releasably coupled. The term "substantially" is defined to be essentially conforming to the particular dimension, shape, or other feature that the term modifies, such that the component need not have that exact feature. The term "comprising," when utilized, means "including, but not necessarily limited to"; it specifically indicates open-ended inclusion or membership in the so-described combination, group, series, and the like.

It should be noted that, when an element is considered to be "fixed to" another element, which can be either directly fixed on another element or indirectly fixed on another element with a centered element. When an element is considered to be "coupled with" another element, which can be either directly coupled with another element or indirectly coupled with another element with a centered element at the same time.

Unless otherwise defined, all technical and scientific terms used herein have the same meaning as commonly understood by one skilled in the art. The terms used in a specification of the present application herein are only for describing specific embodiments, and are not intended to limit the present application. The terms "and/or" used herein includes any and all combinations of one or more of associated listed items.

Figure 2:
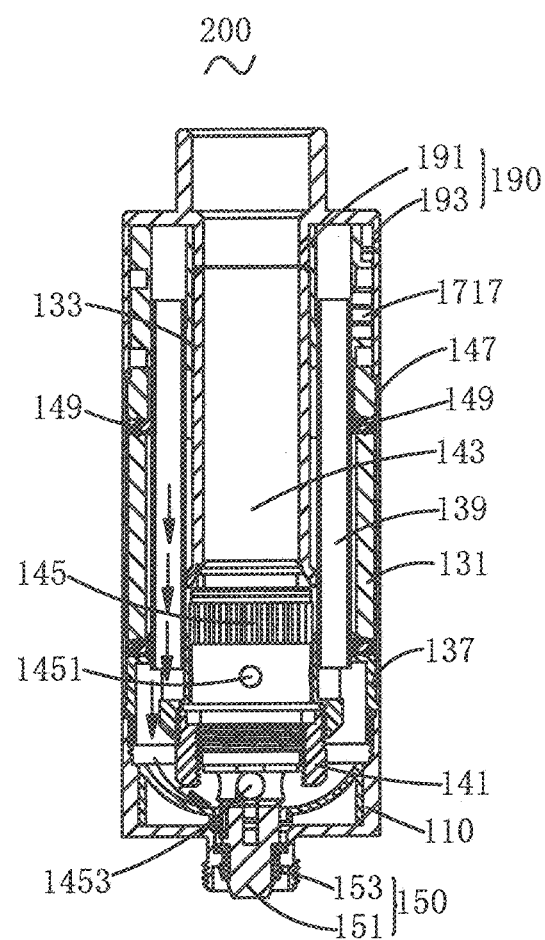
FIG. 2 is a cross-sectional view of the atomizer shown in FIG. 1.

Referring to FIGS. 1-2, the present application provides an atomizer 200, which includes a bottom cover 110, an atomizing assembly 130, a conductive assembly 150, and an adjusting assembly 170.

The atomizing assembly 130 is arranged on the bottom cover 110. The conductive assembly 150 is mounted in the atomizing assembly 130. The adjusting assembly 170 is arranged on the atomizing assembly 130 and in fluid communication with the atomizing assembly 130. The adjusting assembly 170 cooperates with the atomizing assembly 130 for air intake, liquid injection and regulating the air inlet volume.

Figure 3:
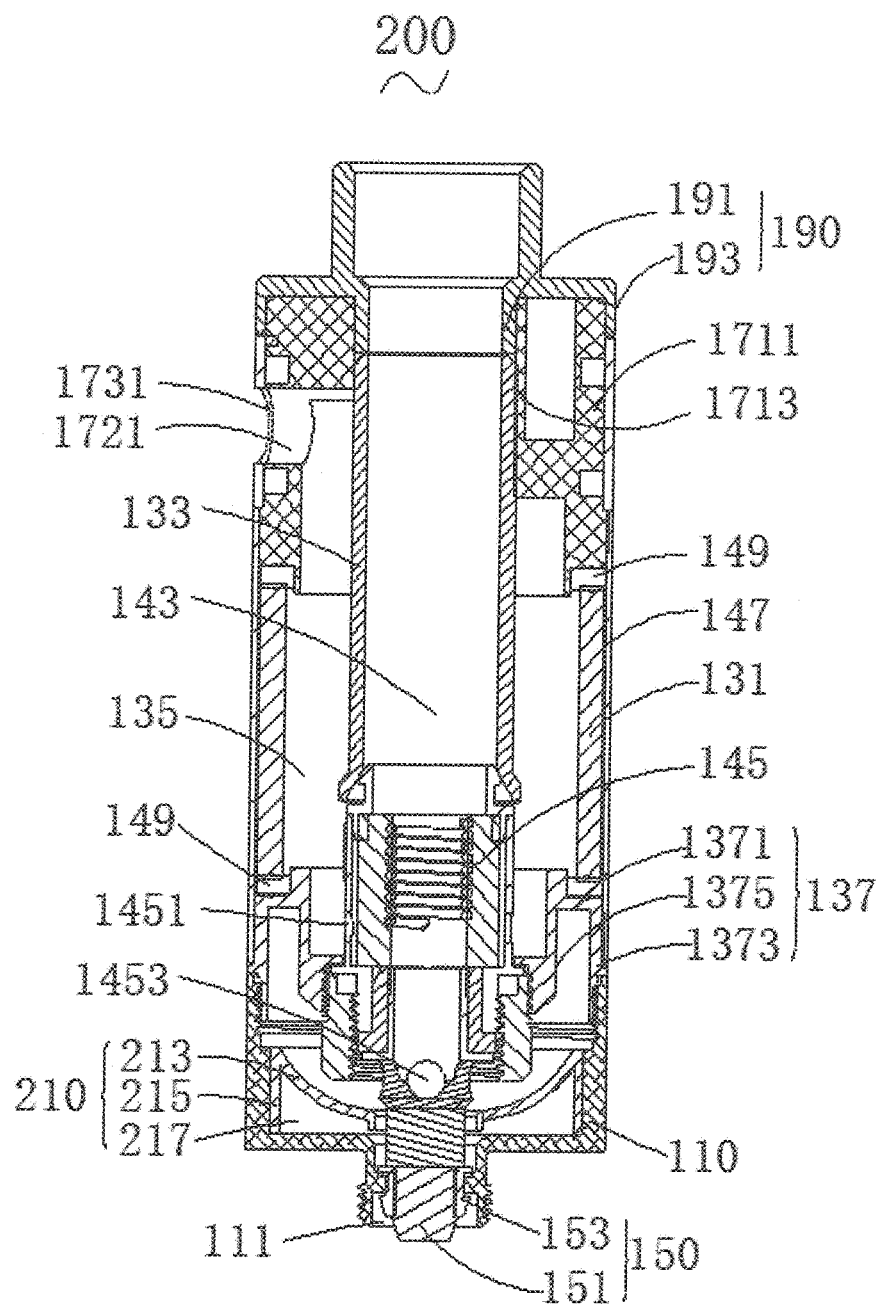
FIG. 3 is a cross-sectional view from another direction of the atomizer shown in FIG. 1.
Figure 4:
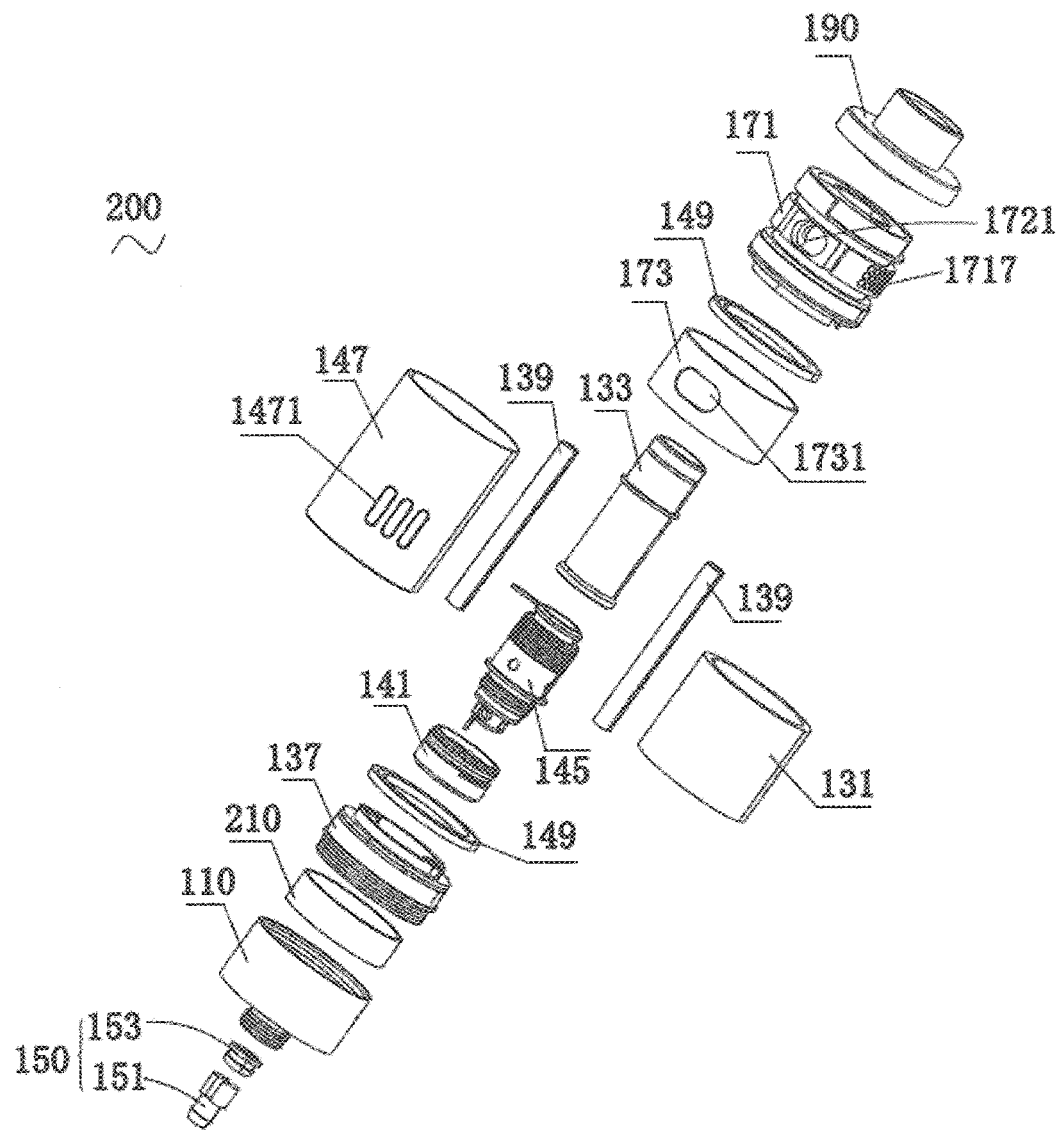
FIG. 4 is a stereoscopic, exploded view of the atomizer shown in FIG. 1.
Figure 5:
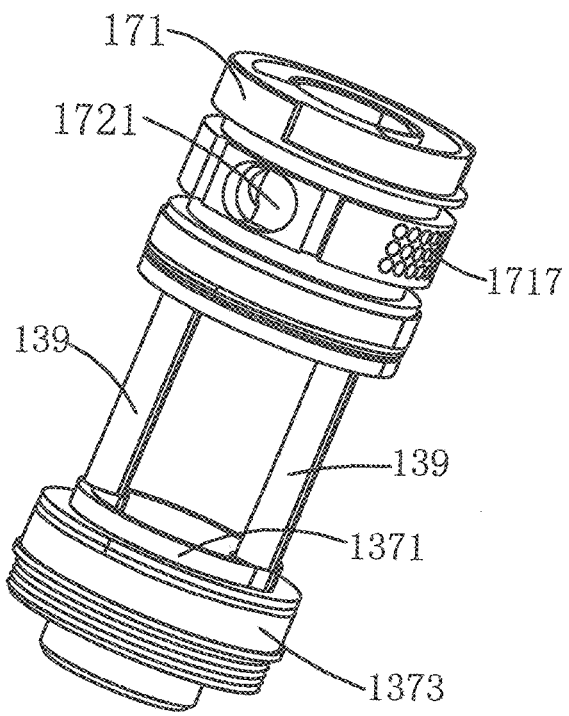
FIG. 5 is a schematic, assembled view of a substrate, an inlet pipe, and a base shown in FIG. 4.
Figure 6:
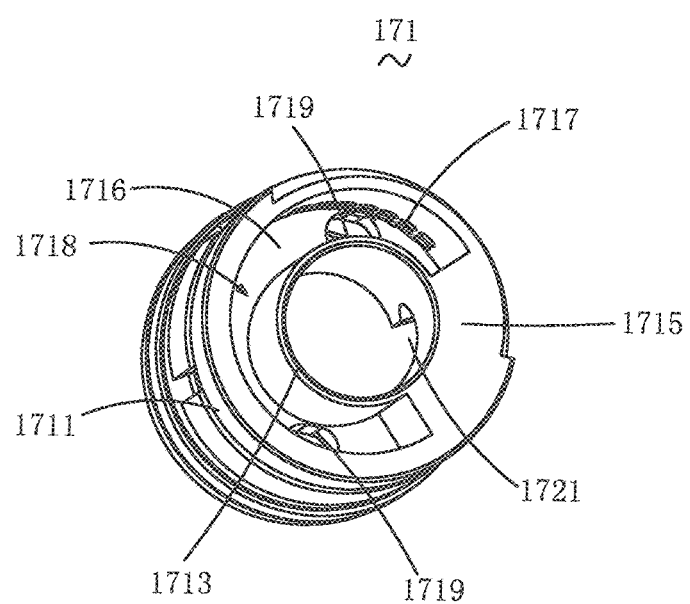
FIG. 6 is a stereoscopic, schematic view of the substrate shown in FIG. 4.
Figure 7:
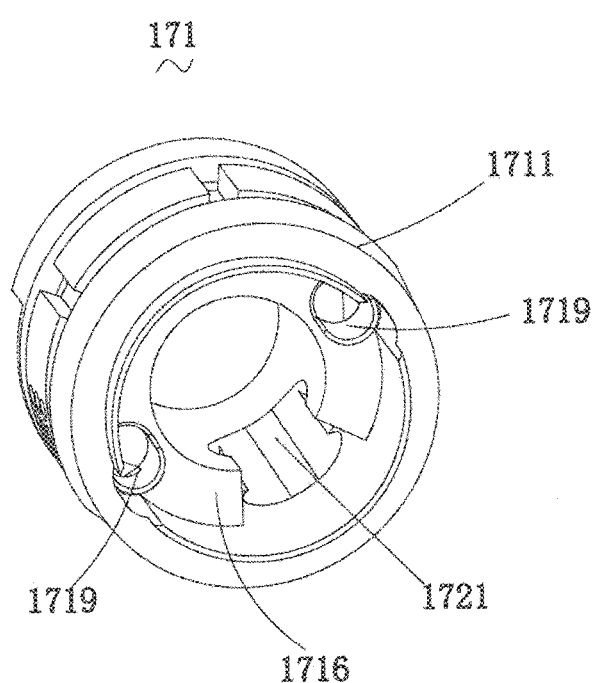
FIG. 7 is a schematic perspective view from another direction of the substrate shown in FIG. 4.
Figure 8:
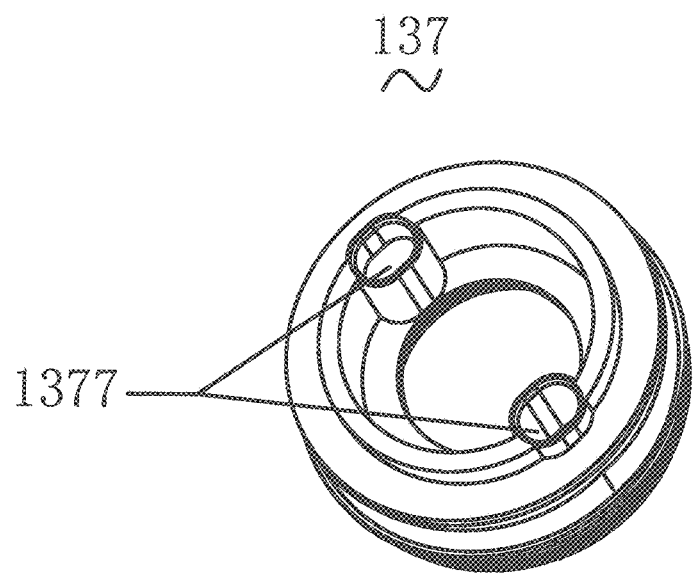
FIG. 8 is a stereoscopic, schematic view of the base shown in FIG. 4.
Figure 9:
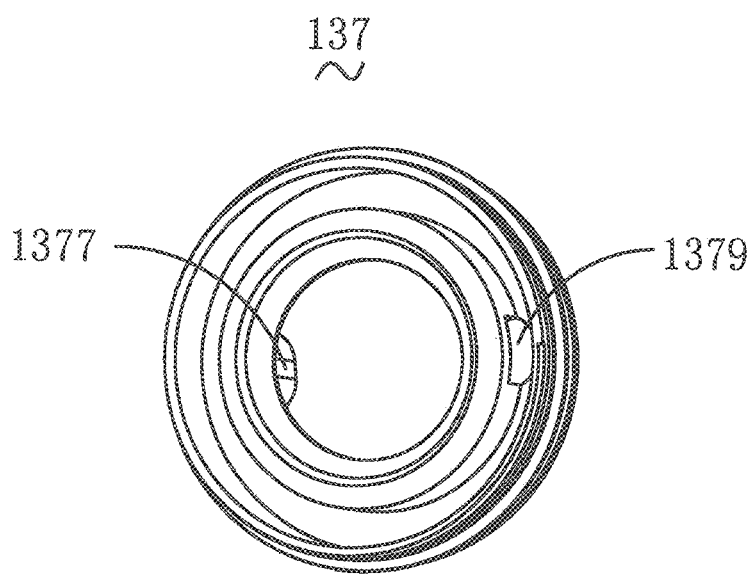
FIG. 9 is a stereoscopic, schematic view from another direction of the base shown in FIG. 4.

Referring to FIGS. 3-5, the atomizing assembly 130 includes an accommodating tube 131, an atomizing tube 133, an accommodating chamber 135, a base 137, an air inlet pipe 139, a connecting ring 141, an atomizing chamber 143, an atomizer head 145, and an outer tube 147. The atomizing tube 133 is arranged within the accommodating tube 131. One end of the atomizing tube 133 is tightly fitted with the atomizer head 145, and an opposite end of the atomizing tube 133 is arranged on the adjusting assembly 170. The atomizer head 145 is screwed on the base 137 by the connecting ring 141. That is, an inside of the connecting ring 141 is screwed on the atomizer head 145, and an outside of the connecting ring 141 is threadedly coupled to the base 137. The accommodating chamber 135 is formed among the accommodating tube 131, the atomizing tube 133, and the base 137. The air inlet pipe 139 is arranged within the accommodating chamber 135. The internal space of the atomizing tube 133 is formed as the atomizing chamber 143.

The outer tube 147 is sleeved on the accommodating tube 131. One end of the outer tube 147 is arranged on the base 137, and an opposite end of the outer tube 147 is arranged on the adjusting assembly 170. In the embodiment, the accommodating tube 131 is made of a transparent or translucent material. The outer tube 147 includes an observing window 1471 for allowing a user to observe a remainder of an aerosol-forming substrate in the accommodating chamber 135.

One end of the accommodating tube 131 is abutted against the adjusting assembly 170, and an opposite end of the accommodating tube 131 is abutted against the base 137, so the accommodating tube 131 is arranged between the base 137 and the adjusting assembly 170. In the embodiment, one seal ring 149 is arranged between the accommodating tube 131 and the adjusting assembly 170, and another is arranged between the accommodating tube 131 and the base 137. The seal rings 149 are configured for improving a sealing property of the accommodating chamber 135, and preventing the aerosol-forming substrate leaking.

The base 137 includes a shoulder 1371, a first connecting portion 1373, and a second connecting portion 1375. The first connecting portion 1373 and the second connecting portion 1375 are coupled to opposite ends of the shoulder 1371, respectively. The first connecting portion 1373 is coupled to the bottom cover 110, and the second connecting portion 1375 is coupled to the connecting ring 141. In the embodiment, the above connection is a threaded connection.

Furthermore, one end of the accommodating tube 131 adjacent to the base 137 is abutted against the shoulder 1371. The accommodating chamber 135 is formed among the accommodating tube 131, the second connecting portion 1375, the atomizer head 145, and the atomizing tube 133. The atomizer head 145 defines a liquid inlet 1451. The aerosol-forming substrate to from aerosol in the accommodating chamber 135 may enter the atomizer head 145 through the liquid inlet 1451.

Referring to FIGS. 2-5, 8 and 9, the base 137 includes two connecting tubes 1377. Each of the connecting tubes 1377 is sleeved and in fluid communication with one of the air inlet pipes 139, respectively. The first connecting portion 1373 defines two through holes 1379. Each of the through holes 1379 is in fluid communication with the connecting tube 1377. The atomizer head 145 defines a ventilating hole 1453 in fluid communication with the through hole 1379. Under the user's suction, air entering the air inlet pipe 139 may enter the atomizer head 145 through the connecting tube 1377, the through hole 1379, and the ventilating hole 1453. The air would take away an atomized aerosol formed by the atomizer head 145.

The bottom cover 110 defines a connecting hole 111. The conductive assembly 150 passing through the connecting hole 111 is in electrical contact with the atomizer head 145 and a power source (not shown). Specifically, the conductive assembly 150 includes a positive contacting member 151 and an insulating member 153. The insulating member 153 is sleeved on the positive contacting member 151. One end of the positive contacting member 151 is electrically connected to the atomizer head 145, and an opposite end of the positive contacting member 151 passing through the connecting hole 111 is electrically connected to the power source for supplying electric power to the atomizing assembly 130.

Referring to FIGS. 2, 3, 6 and 7, the adjusting assembly 170 is configured for air intake, liquid injection and regulating the air inlet volume, and the like of the atomizer 200. The adjusting assembly 170 includes a substrate 171 and an adjusting member 173. The adjusting member 173 is rotatably sleeved on the substrate 171, and the substrate 171 limits a movement of the adjusting member 173 in an axial direction of the substrate 171. In the embodiment, the adjusting member 173 is an adjusting ring rotatably sleeved on the substrate 171.

The substrate 171 includes a main body 1711, an inner tube 1713, a separator 1715, and a splitter plate 1716. The separator 1715 is coupled to the splitter plate 1716. The separator 1715 and the splitter plate 1716 are arranged between the main body 1711 and the inner tube 1713, and are fixedly coupled to the main body 1711 and the inner tube 1713 respectively.

The main body 1711 is substantially a tube body, which includes at least one air inlet 1717. The inner tube 1713 is arranged in the main body 1711, and sleeved on the atomizing tube 133.

The main body 1711 further defines an injecting hole 1721. The injecting hole 1721 extends through the inner tube 1713 and is in fluid communication with the accommodating chamber 135. The aerosol-forming substrate may be introduced into the accommodating chamber 135 through the injecting hole 1721. In the embodiment, the injecting hole 1721 and the air inlet 1717 are arranged on a circumference of the same cross section of the substrate 171.

The separator 1715 is laminated on the splitter plate 1716. The separator 1715 is arranged between the main body 1711 and the inner tube 1713, to allow the main body 1711 to be coupled to the inner tube 1713. In the embodiment, the separator 1715 is substantially a sector-ring body.

The splitter plate 1716 is substantially annular. The injecting hole 1721 passes through the splitter plate 1716. The splitter plate 1716 defines two mounting holes 1719 in fluid communication with the air inlet 1717. One end of each air inlet pipe 139 adjacent to the adjusting assembly 170 is mounted in one of the mounting holes 1719.

The air inlet 1717 is defined in a region where the main body 1711 is not fixedly connected to the splitter plate 1716 and the separator 1715. The air inlet 1717 is in fluid communication with the air inlet channel 1718 formed among the splitter plate 1716, the main body 1711, the inner tube 1713, and the separator 1715. The mounting holes 1719 is in fluid communication with the air inlet channel 1718, so that the air inlet pipe 139 mounted in the mounting hole 1719 is in fluid communication with the air inlet 1717. The injecting hole 1721 penetrates through the main body 1711, a part of a laminated area formed between the separator 1715 and the splitter plate 1716, and the inner tube 1713. The inner tube 1713 separates the air inlet 1717 from the injecting hole 1721.

The atomizer 200 further includes a cigarette holder base 190. The cigarette holder base 190 is sleeved on the adjusting member 173. The cigarette holder base 190 includes a smoke outlet tube 191 and a cover body 193 extending outward from the smoke outlet tube 191. The smoke outlet tube 191 is tightly coupled to and in fluid communication with the atomizing tube 133. The inner tube 1713 is sleeved on the smoke outlet tube 191 and the atomizing tube 133. The cover body 193 covers one end of the adjusting assembly 170 opposite to the atomizing assembly 130, and the cover body 193 is tightly engaged with the main body 1711. In this way, under the cooperation between the separator 1715 and the cigarette holder base 190, the air inlet channel 1718 is separated from an injecting channel (not labeled, formed among the main body 1711, the smoke outlet tube 191, and the atomizing tube 133), so the air can enter the air inlet pipe 139 through the air inlet 1717 directly and cannot enter the accommodating chamber 135.

The adjusting member 173 defines an adjusting window 1371 in fluid communication with the air inlet 1717.

An actual size of the air inlet 1717 at the air intake can be adjusted by rotating the adjusting member 173 (which rotates the adjusting window 1731 fixed thereof). During the rotation of the adjusting member 173, the air inlet 1717 is shielded by the adjusting member 173 or exposed through the adjusting window 1731. The larger the exposed portion of the air inlet 1717, the greater is the size of the actual intake air for the air inlet 1717. The smaller the exposed portion of the air inlet 1717, the smaller is the size of the actual intake air for the air inlet 1717.

It should be noted that there may be multiple air inlets 1717. When there is more than one air inlet 1717, the size of each of the air inlets 1717 may be the same or different.

It should be noted that the air inlet 1717 can be wholly or partially overlapped the adjusting window 1731 when the adjusting member is in rotation, so the atomizer 200 may have an adjustable air intake function. In another embodiment, the number and shape of the air inlet 1717 and the adjusting window 1731 may set according to actual needs, and not particularly limited.

In another embodiment, the adjusting member 173 may be an adjusting sheet latched on an edge of the substrate 171, and the adjusting sheet may rotate along the edge of the substrate. The injecting hole 1721 and/or the air inlet 1717 are shielded or exposed during the adjusting sheet in rotation.

It should be noted that, the adjusting member 173 is movably arranged on the substrate 171 based on an actual shape of the atomizer 200, and may be not limited to being rotatably and slidably arranged on the substrate 171. The term "slidable" is defined as going up and down, left and right, and other movement around the substrate 171.

Figure 10:
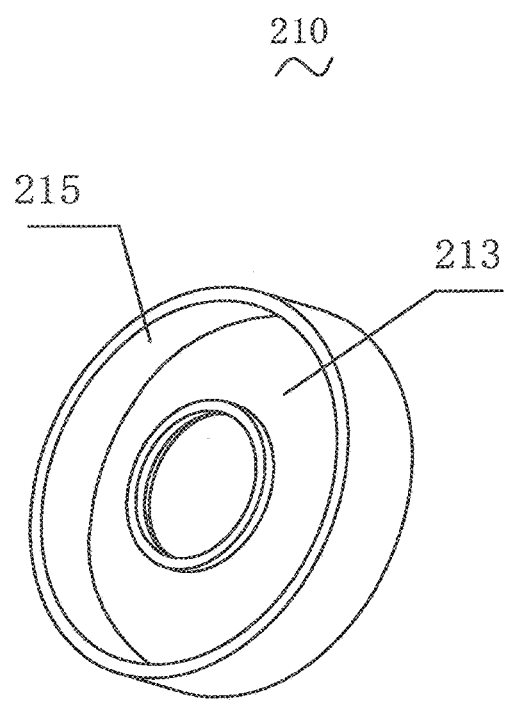
FIG. 10 is a stereoscopic, schematic view of a collecting device shown in FIG. 4.
Figure 11:
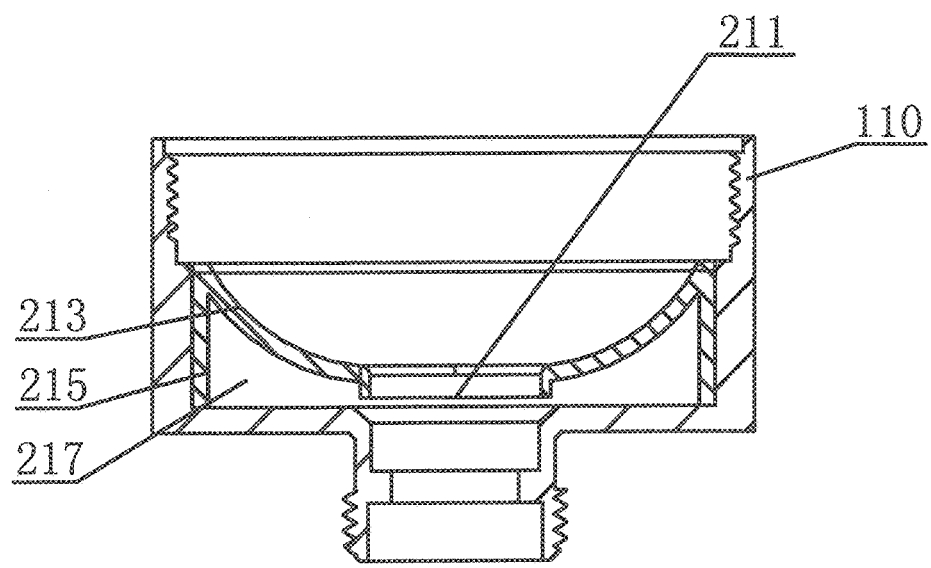
FIG. 11 is a schematic cross-sectional view of the collecting device and a bottom cover shown in FIG. 4.

Furthermore, the atomizer 200 also includes a collecting device 210. Referring to FIGS. 3, 10 and 11, the collecting device 210 is arranged on the bottom cover 110, which is configured for collecting the aerosol-forming substrate leaking from the atomizer head 145 and the accommodating chamber 135, a condensed aerosol, or other liquid. The collecting device 210 defines an engaging hole 211. The conductive assembly 150, which passes through the engaging hole 211 and the connecting hole 111 in turn, is electrically contacting the power source. A gap is formed between the engaging hole 211 and the conductive assembly 150, which is configured for the aerosol-forming substrate, the condensed aerosol or other liquid to flow into a space formed between the collecting device 210 and the bottom cover 110. In this way, the leakage of the atomizer 200 is avoided.

The collecting device 210 includes a stagnating portion 213, a tube 215, and a collecting slot 217. The stagnating portion 213 is substantially a bowl-like body or a funnel body extending from an upper end of the tube 215 to an inside of the tube 215. That is, the stagnating portion 213 is substantially in a shape of a bowl or a funnel. The engaging hole 211 is defined in a center of the stagnating portion 213. The stagnating portion 213 and the tube 215 are fixedly coupled together to form the collecting slot 217. An inner wall of the stagnating portion 213 and an inner wall of the tube 215 constitute a groove wall of the collecting slot 217. When the atomizer 200 is inverted, liquid flows to a bottom of the collecting slot 217, so the liquid can be prevented from flowing back to the atomizer head 145 or the accommodating chamber 135.

In the embodiment, an angle is formed between the tube 215 and the stagnating portion 213. The angle is substantially in a range from 0 to 90 degrees.

The atomizer 200 has following advantages:

First, the adjusting assembly has functions for air intake, liquid injection, regulating the air inlet volume and the like, so as to simplify a structure of the atomizer and shorten a length of the atomizer.

Second, the adjusting assembly is located at a top end of the atomizer at a position close to an inhaler. That is, air enters the atomizer through an air inlet arranged on the top end of the atomizer, rather than through a conventional air inlet arranged on a bottom end of the atomizer, so the bottom end of the atomizer of the present application needs not to define an air inlet. That is, the bottom end of the atomizer is sealed, so the aerosol-forming substrate is prevented from leaking out.

Third, liquid is injected into a top end of the atomizer through the injecting hole, a leakage problem caused by a detachable connection between the atomizing assembly and the bottom cover is avoided.

Fourth, the atomizer has a simple structure, and the device is not complex to be leak-proof.

Fifth, the atomizer has the air inlet and the injecting hole arranged on the top end of the atomizer, so the leakage of the atomizer can be avoided.

Sixth, the collecting device can further avoid the leakage of the atomizer.

The present application also provides an aerosol generating device having the atomizer 200.

The embodiments shown and described above are only examples. Many details are often found in the art such as the other features of atomizers. Therefore, many such details are neither shown nor described. Even though numerous characteristics and advantages of the embodiments have been set forth in the foregoing description, together with details of the structure and function of the embodiments, the present disclosure is illustrative only, and changes may be made in details, including in the matters of shape, size, and arrangement of parts within the principles of the embodiments to the full extent indicated by the broad general meaning of the terms in which the appended claims are expressed.

What is claimed is:

1. An atomizer comprising:
   an atomizing assembly, and
   an adjusting assembly arranged on an upper end of the atomizing assembly,
   wherein the atomizing assembly comprises an atomizer head and an air inlet pipe, wherein the adjusting assembly comprises a substrate, the substrate comprises a main body, an inner tube, a separator, and a splitter plate, wherein the inner tube is located in the main body, the separator is laminated on the splitter plate, the separator and the splitter plate are arranged between the main body and the inner tube, and the separator and the splitter plate are respectively fixedly coupled with the main body and the inner tube, wherein the main body defines an air inlet in fluid communication with the outside, one end of the air inlet pipe is in fluid communication with a bottom of the atomizer head, and wherein the other end of the air inlet pipe is in fluid communication with the air inlet.

2. The atomizer of claim 1, wherein the atomizing assembly further comprises a base, wherein the base is disposed with a connecting tube and a through hole in fluid communication with the connecting tube, wherein the bottom of the atomizer head defines a ventilating hole in fluid communication with the through hole, wherein one end of the air inlet pipe is sleeved within the connecting tube, wherein the air inlet pipe is in fluid communication with the ventilating hole by the through hole, and wherein air enters the air inlet pipe through the air inlet, and then enters the atomizer head through the connecting tube, the through hole, and the ventilating hole.

3. The atomizer of claim 2, wherein the splitter plate of the substrate defines a mounting hole, wherein the mounting hole is in fluid communication with the air inlet, and wherein the other end of the air inlet pipe is mounted in the mounting hole.

4. The atomizer of claim 3, wherein the adjusting assembly further comprises an adjusting member arranged rotatably related to the substrate, wherein the adjusting member includes an adjusting window, and wherein the air inlet is shielded by the adjusting member or exposed through the adjusting window when the adjusting member is in rotation.

5. The atomizer of claim 4, wherein the atomizing assembly further comprises an accommodating chamber for accommodating an aerosol-forming substrate, wherein the substrate of the adjusting assembly defines an injecting hole opposite to the air inlet, wherein the injecting hole is in fluid communication with the accommodating chamber, thereby allowing the aerosol-forming substrate to be introduced into the accommodating chamber through the injecting hole, and wherein the injecting hole is shielded by the adjusting member or exposed through the adjusting window when the adjusting member is in rotation.

6. The atomizer of claim 5, wherein an air inlet channel is formed among the main body, the inner tube, the separator and the splitter plate, the air inlet channel is in fluid communication with the air inlet and the mounting hole, and wherein the injecting hole penetrates through the main body, through a part of a laminated area formed between the separator and the splitter plate, and through the inner tube.

7. The atomizer of claim 2, wherein the atomizing assembly further comprises a connecting ring, an inside of the connecting ring is coupled to the atomizer head, and wherein an outside of the connecting ring is coupled to the base.

8. The atomizer of claim 1, wherein the atomizer further comprises a bottom cover and a collecting device, wherein the bottom cover is arranged on a bottom end of the atomizer head, the collecting device is arranged on the bottom cover and located between the bottom cover and the atomizer head, wherein the collecting device comprises a stagnating portion, a tube, and a collecting slot, wherein one end of the tube extends to an inside of the tube to form the stagnating portion, wherein the stagnating portion is fixedly coupled with the tube to form the collecting slot, and wherein an angle formed between the tube and the stagnating portion is in a range from 0 to 90 degrees.

9. The atomizer of claim 8, wherein the stagnating portion is in a shape of a bowl or a funnel.

10. An aerosol generating device, comprising:
    an atomizer, comprising:
       an atomizing assembly, and
       an adjusting assembly arranged on an upper end of the atomizing assembly,
       wherein the atomizing assembly comprises an atomizer head and an air inlet pipe, wherein the adjusting assembly comprises a substrate, the substrate comprises a main body, an inner tube, a separator, and a splitter plate, wherein the inner tube is located in the main body, the separator is laminated on the splitter plate, the separator and the splitter plate are arranged between the main body and the inner tube, and the separator and the splitter plate are respectively fixedly coupled with the main body and the inner tube, wherein the main body defines an air inlet in fluid communication with the outside, one end of the air inlet pipe is in fluid communication with a bottom of the atomizer head, and wherein the other end of the air inlet pipe is in fluid communication with the air inlet.

11. The aerosol generating device of claim 10, wherein the atomizing assembly further comprises a base, wherein the base is disposed with a connecting tube and a through hole in fluid communication with the connecting tube, wherein the bottom of the atomizer head defines a ventilating hole in fluid communication with the through hole, wherein one end of the air inlet pipe is sleeved within the connecting tube, wherein the air inlet pipe is in fluid communication with the ventilating hole by the through hole, and wherein air enters the air inlet pipe through the air inlet, and then enters the atomizer head through the connecting tube, the through hole, and the ventilating hole.

12. The aerosol generating device of claim 11, wherein the splitter plate of the substrate defines a mounting hole, wherein the mounting hole is in fluid communication with the air inlet, and wherein the other end of the air inlet pipe is mounted in the mounting hole.

13. The aerosol generating device of claim 12, wherein the adjusting assembly further comprises an adjusting member arranged rotatably related to the substrate, wherein the adjusting member includes an adjusting window, and wherein the air inlet is shielded by the adjusting member or exposed through the adjusting window when the adjusting member is in rotation.

14. The aerosol generating device of claim 13, wherein the atomizing assembly further comprises an accommodating chamber for accommodating an aerosol-forming substrate, wherein the substrate of the adjusting assembly defines an injecting hole opposite to the air inlet, wherein the injecting hole is in fluid communication with the accommodating chamber, thereby allowing the aerosol-forming substrate to be introduced into the accommodating chamber through the injecting hole, and wherein the injecting hole is shielded by the adjusting member or exposed through the adjusting window when the adjusting member is in rotation.

15. The aerosol generating device of claim 14, wherein an air inlet channel is formed among the main body, the inner tube, the separator and the splitter plate, the air inlet channel is in fluid communication with the air inlet and the mounting hole, and wherein the injecting hole penetrates through the main body, through a part of a laminated area formed between the separator and the splitter plate, and through the inner tube.

* * * * *